United States Patent [19]

Sanford et al.

[11] Patent Number: 5,045,208
[45] Date of Patent: Sep. 3, 1991

[54] COLUMN ANALYZER SYSTEM

[75] Inventors: James R. M. Sanford, Vidor; Patrick M. Frank, Beaumont; Joseph H. Golias, Beaumont; William C. Jennings, Beaumont, all of Tex.

[73] Assignee: Helena Laboratories Corporation, Beaumont, Tex.

[21] Appl. No.: 427,346

[22] Filed: Oct. 27, 1989

[51] Int. Cl.$^5$ .............................................. B01D 15/08
[52] U.S. Cl. .................................. 210/656; 210/198.2; 73/61.1 C; 422/70; 436/161; 436/809
[58] Field of Search ...................... 210/656, 659, 198.2, 210/657; 73/61.1 C; 436/161, 809; 422/70; 55/386

[56] References Cited

U.S. PATENT DOCUMENTS

4,341,635 7/1982 Golias ................................. 210/656
4,604,198 8/1986 Dailey et al. ...................... 210/198.2

Primary Examiner—Stanley Silverman
Assistant Examiner—Neil M. McCarthy
Attorney, Agent, or Firm—Spencer & Frank

[57] ABSTRACT

An analyzer system for automatic column chromatography, and method for its use, includes an array of chromatograph columns and multi-cell cuvettes associated with each column. Chromatographic separation takes place under a constant, low fluid pressure. A pressure system distributes air to each column during chromatographic separation but prevents leakage of air if the column array is partially empty. The multi-cell cuvette collects and separates the eluates associated with a single column. The system provides for automatic removal of caps from the bottoms of the chromatograph columns and provides for automatic optical density reading.

19 Claims, 7 Drawing Sheets

COLUMN ANALYZER SYSTEM

BACKGROUND OF THE INVENTION

This invention relates to column chromatography and, more particularly, to an improved column analyzer system which provides for automatic column chromatography and automatic optical density processing.

Column chromatography (often called microchromatography) is a well-known technique utilized as part of clinical chemistry for analyzing the various constituents of fluids such as blood. For example, Helena Laboratories Corporation, the assignee of the present invention, has marketed equipment and accessories for column chromatography as well as photometers or optical readers. Patent literature relating to column chromatography includes, for example, U.S. Pat. No. 4,341,635 issued July 27th, 1982 to Tipton Golias and assigned to Helena Laboratories Corporation (as well as the prior art cited therein), and there is commercially available equipment relative to automating one or more aspects of column chromatography. For example, at least one machine has been marketed prior to the present invention which automates the introduction of fluids into a chromatograph column, and the collection of the eluates from the column. Such equipment also provides for the processing of a plurality of chromatograph columns which are arranged in an array or matrix within the equipment.

The prior art, however, suffers from numerous disadvantages and shortcomings relative to the safe, accurate and expeditious chromatographic processing and subsequent optical density readings.

For example, according to the prior art, the eluate solutions are collected in a series of cuvettes, one cuvette for each eluate solution or fraction. Thereafter, the cuvettes are sequentially processed in an optical reader. This technique is time consuming, permits errors in identification of the cuvettes and exposes the technician handling the cuvettes to biological hazards such as HIV virus which may be carried in the blood specimens. The equipment which automates the processing of columns has heretofore discharged the eluates into a series of test tubes, and then the technician or operator of the equipment must manually transfer the contents into a series of cuvettes since test tubes, because of their curvature, are not amenable to optical density reading.

While extremely high pressure liquid chromatography (HPLC) is well known, and while pressurized chromatography is known based upon the aforementioned Golias U.S. Pat. No. 4,341,635, we have discovered that a constant low pressure greatly enhances liquid chromatography. Prior to the present invention, however, constant low pressure liquid chromatography was not available.

SUMMARY OF THE INVENTION

The present invention overcomes the shortcomings of the prior art by providing a new and improved column analyzer system and method.

The column analyzer system of the present invention provides for the automated processing of an array of chromatographic columns, including removal of caps from the columns, without technician intervention and which provides for the follow-up optical density reading of the eluted solutions.

The present invention provides for an automatic removal of the protective cap at the bottom of the chromatograph column and provides for elution of liquid fractions into a new and improved cuvette such that a single cuvette will contain, in separate cells, the eluates and the total fraction.

The present invention further provides for constant, low pressure on each column during the chromatographic process through the use of a new and improved pressure system.

BRIEF DESCRIPTION OF THE DRAWINGS

The foregoing objects and advantages of the present invention, together with other advantages which may be obtained by its use, will become more apparent reading the following detailed description of the invention taken in conjunction with the drawings.

In the drawings, wherein like reference numerals identify corresponding components:

FIG. 5, comprising

DETAILED DESCRIPTION OF THE INVENTION

Figure 1:
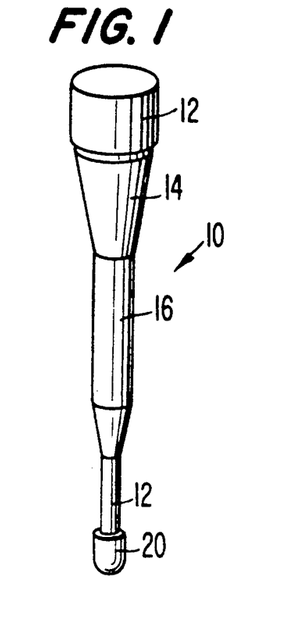
FIG. 1 is an illustration of a chromatograph column according to the principles of the present invention.
Figure 4:
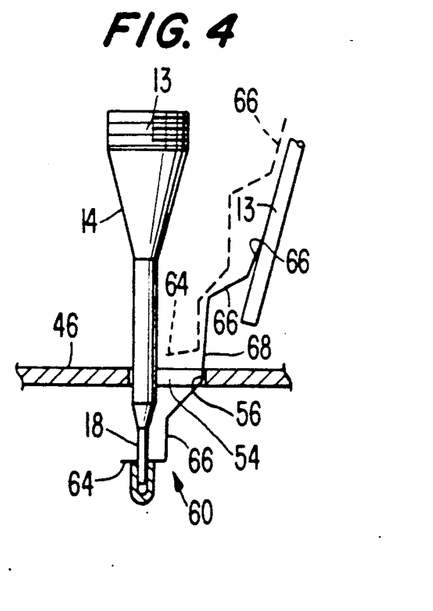
FIG. 4 illustrates in section the apparatus for removing the caps from the chromatograph columns.

With reference to the drawings, FIG. 1 illustrates a conventional chromatograph column 10 which includes a upper end or cover 12 threadingly engaged onto the body portion of the column. The body portion of the column includes a downwardly and inwardly tapering reservoir portion 14 communicating with a barrel portion 16 which barrel portion contains ion exchange resin particles. The lower end of the barrel portion 16 tapers downwardly to a tip portion 18 which is covered by a removable cap 20. The column 10 as described and illustrated, including a threadable cover 12 (threads 13 are shown in FIG. 4), is conventional.

During liquid chromatography, it has been conventional, prior to the present invention, for the eluates to be discharged into a series of cuvettes or a series of test tubes. When test tubes are used, the contents are subsequently transferred into cuvettes since the curvature of the body of a test tube interferes with the optical density reading. A cuvette, with its generally flat walls, avoids the problem of distortion of the optical density. However, prior to the present invention, each of the eluates from a chromatographic process have been collected in discrete cuvettes leading to the risk of errors in the processing of the individual cuvettes.

Figure 2:
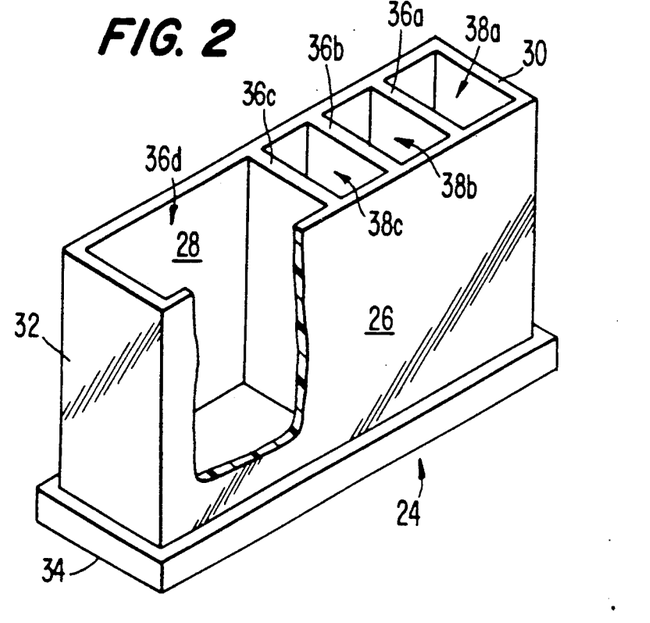
FIG. 2 is a perspective illustration, partially broken away, of the cuvette of the present invention.

The present invention provides an improved cuvette means 24 which provides for the collection of all of the eluates from a single column within separate cells of a single cuvette means. With reference to FIG. 2, the cuvette means 24 is a generally rectangular container having opposed, parallel, spaced-apart side walls 26, 28, and opposed, spaced-apart parallel end walls 30, 32 oriented perpendicular to the side walls. The side walls and end walls of the cuvette means are mounted on a base 34, and the side walls and end walls, together with the base, define a rectangular container which is open at the top and closed at the bottom.

By way of example, but not by way of limitation, the cuvette means may include four separate cells. Three interior walls 36a,b,c extend between the side walls 26, 28, with the interior walls being generally parallel to the end walls 30, 32. The cuvette means thus defines four discrete cells 38a,b,c,d, respectively. Each cell is defined by the base 34, the side walls 26, 28, and two additional walls. In the case of cell 38a, the two additional walls are walls 30 and 36a; for cell 38b, the two additional walls are walls 36a and 36b. The two additional walls which define cell 38c are interior walls 36b and 36c. The two additional walls which define cell 38d are walls 36c and 32. It should be noted that cells 38a,b,c are of generally equal size and are substantially smaller than cell 38d for reasons which will be hereinafter explained.

Figure 3:
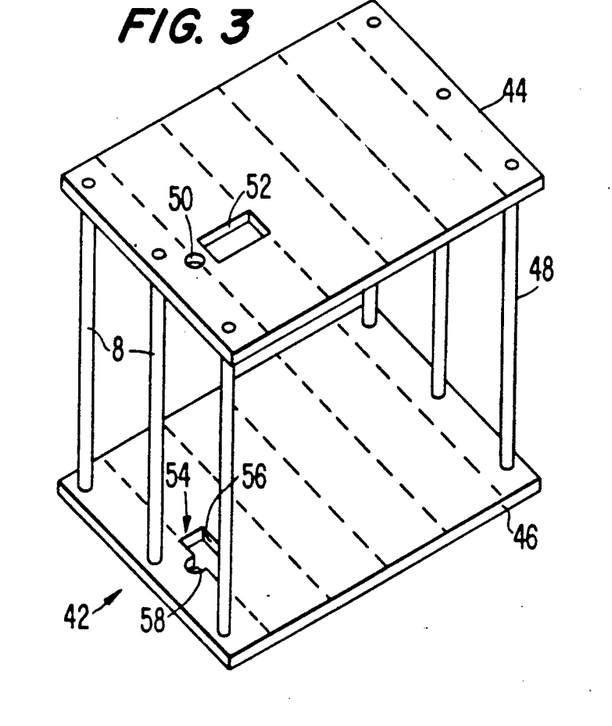
FIG. 3 illustrates, in perspective view, a rack for supporting a plurality of chromatograph columns according to the principles of the present invention.

Referring to FIGS. 3, a rack 42 is provided for supporting an array of columns. The rack includes upper and lower plates 44, 46, respectively, supported and maintained in spaced-apart relationship by a plurality of cylindrical rods 48. In the present embodiment of the invention, the upper and lower plates support 50 columns in a 5×10 array. The upper plate 44 is provided with a series of circular apertures 50 of a size and shape to receive the barrel 16 of the column 10. Adjacent each circular aperture is a rectangular aperture 52 to accommodate the automatic column cap removal means which will hereafter be explained. The lower plate 46 includes a plurality of apertures 54 which are generally rectangular in configuration. Each generally rectangular aperture 54 includes opposed short walls, a first longer wall 56 interconnecting the short walls, and a second wall 58 opposed from the longitudinal wall 56 which second wall includes a generally circular cutout portion. The diameter of the generally circular cutout portion is configured to support the lower end of the barrel 16 of the column, and is aligned under the circular aperture 50 in the upper plate, and the longitudinal wall 56 is a bearing surface for the automatic cap removal. In FIG. 3, only a single set of apertures in plate 44 is illustrated although 50 such sets, in a 5×10 array are contemplated. Similarly, only a single aperture 54 is illustrated in plate 46 although a 5×10 array is contemplated. The rack is positioned at a first station in the apparatus of the present invention.

Figures 5A, 5B, 5C:
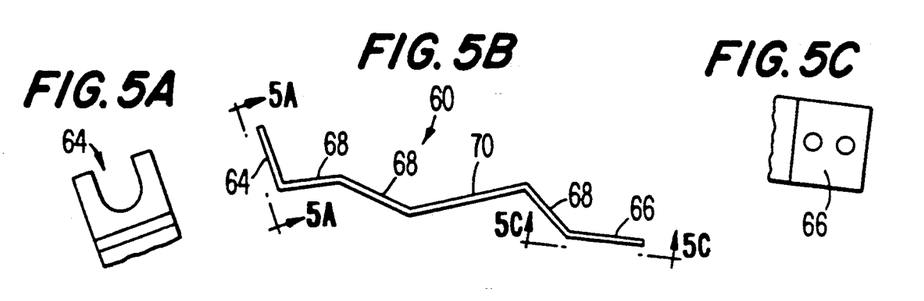
FIGS. 5A, 5B and 5C, illustrates the cap removal means with elevation views of each end thereof and with an edge view thereof.

After the chromatography columns are loaded into the rack and placed in position at the first station in the apparatus of the present invention, means are provided for automatically removing the cap 20 from the lower end of each column. FIG. 4 illustrates two positions of the cap removal means, a rest position illustrated by dashed lines and an active position illustrated by solid lines. Specifically, the automatic cap removal means 60 is an elongated, thin, stainless steel spring strip extending generally vertically through the rectangular portions of the apertures 52, 54 in the upper and lower plates of the rack 42. As also illustrated in FIG. 5, the elongated, thin, steel spring includes a fork portion 64 at the lower end, an apertured upper end 66 for attachment to an actuating mechanism and a series of intermediate portions 68 therebetween, one of which intermediate portions 70 bears against the bearing surface wall 56 as the cap removal means is moved vertically downward within the rack 42. Of course, one cap removal means is provided for each column within the array. Actuating mechanism 139 is attached to the spring by screws extending through the apertures in spring end 66. As the actuating mechanism moves the spring 60 vertically downward, section 70 bears against the longitudinal wall 56 in the lower plate 46. The continued downward movement of the spring against the bearing surface 56 urges the fork means to the left as illustrated in FIG. 4 to engage the tip 18 of the column between the fork tines. The continued downward movement of the spring continues the biasing of the fork 64 against the tip such that the underside of the fork engages the top of the cap 20 and forces the cap downwardly until the cap is free of the column. The cap will, in practice, be retained in the first cell 38a of the cuvette means. Thereafter, the cap removal means is withdrawn vertically upwardly.

Means are provided for automating the column chromatography processing including such steps as applying hemolysate to the sample, agitating the column, running a buffer through the column, thereafter adding the sample to the column, adding the reagent to the column, etc. In general terms, this automatic technique is part of the prior art. However, the present invention includes certain features which are not found in the prior art, namely, the provision of constant, low pressure for the chromatography columns which are being processed. The pressure system will now be explained.

Figure 6:
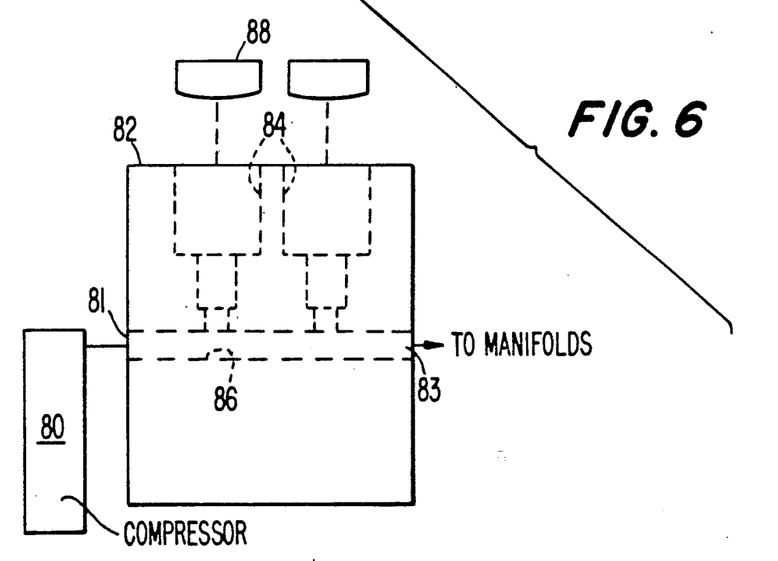
FIGS. 6 and 7 illustrate the system for supplying constant, low pressure including a pressure regulator.
Figure 7:
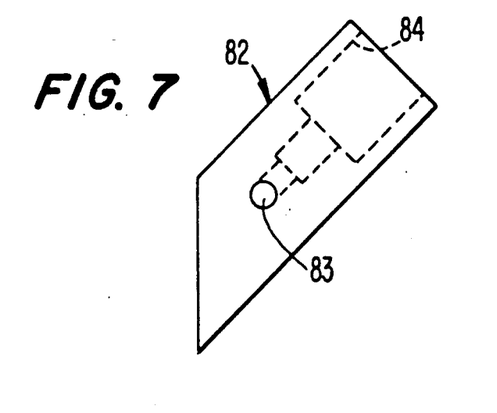

Referring to FIGS. 6 and 7, the pressure system includes a compressor 80 for providing constant air pressure to an input port 81 of a regulator 82. The regulator 82 also includes an output port 83.

The regulator 82 includes two pressure relief bores 84, each of which is generally T-shaped in cross section and each of which communicates with a main conduit 86 such that air from the compressor 80 flows through the input port 81, through the main conduit 86 and through the output port 83 of the regulator. The two relief bores 84 are provided to permit operation of the regulator at two different constant pressures. For this purpose, each relief bore is provided with a projectile shape plunger 88, the plunger in one relief bore being of a different weight than the plunger in the other relief bore. In addition, each relief bore 84 may be selectively closed at the exterior surface thereof such that only one relief bore will be in use at any given time. FIG. 7 illustrates the orientation of the regulator 82 when in use. It will be noted that relief bores 84 are positioned at an angle relative to the vertical axis. In operation, with the plungers mounted within the respective relief bores and with one of the relief bores open and the other closed, if the air pressure through the conduit exceeds a threshold as determined by the weight of the plunger associated with the open relief bore, the air will move the respective plunger upwardly, thus opening a fluid flow path through the relief bore thus providing for a bleed of air pressure. When sufficient air pressure bleeds out through the relief bore, the plunger drops back to seal the relief bore from the main conduit. Positioning the plungers in bores 84 at an angle to the vertical facilitates movement of the plungers.

According to the principles of the present invention, a low but constant air pressure should be maintained at the output port 83, which low pressure should range from about 3 inches of water to about 8 inches of water, depending upon the particular column chromatographic test. Thus, within that range, the weights of the two plungers may be selected such that one plunger is sufficiently light so as to permit a constant air pressure equivalent to three inches of water, and the second plunger is slightly heavier, thus permitting a constant air flow pressure at eight inches of water. It should be further appreciated that it is within the spirit and scope of the present invention to modify the air pressure while still providing constant, low pressure and thus the range of three - eight inches of water as the measurement of the air pressure is illustrative. Slightly less than three inches and slightly more than eight inches may be utilized while achieving the objectives of the present invention.

Figure 8:
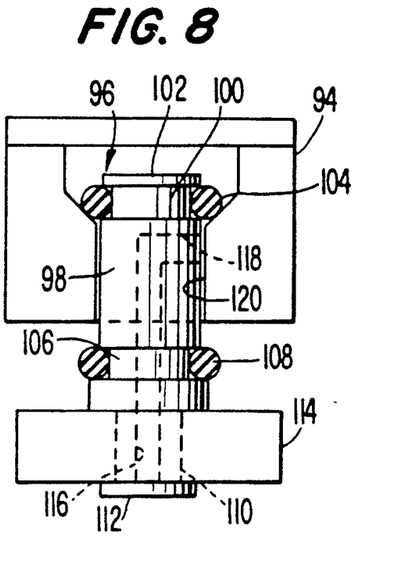
FIG. 8 illustrates the pressure tip associated with a single chromatograph column in a first position disengaged from a column.

Referring next to FIG. 8, it should be remembered that the columns are provided in an array, heretofore described as a 5×10 array, namely, 10 chromatograph columns in each of 5 rows. The output from the pressure regulator 82 is coupled through tubes 93 to each of five manifolds 94, each associated with one row. Each manifold 94 is connected to a pressure tip system of the present invention for providing the desired pressure to each of the chromatograph columns while, at the same time, preventing leakage of air if less than a full array of columns is being processed by the system. The pressure tip system, as illustrated in FIG. 8 in the absence of a chromatograph column, includes an upper block or manifold 94 having a conduit 96 therethrough in fluid communication through tube 93 with the output 83 of the pressure regulator. Mounted partially within the block 94 is an elongated pressure cylinder 98, of generally circular cross section, having three reduced diameter circumferential recesses machined therein. Specifically, cylinder 98 has an upper grove or recess 100 machined therein, the upper groove positioned inwardly of a flange 102. An O-ring seal 104 is positioned within the groove 100. A second groove 106 is provided intermediate the two ends of the cylinder 98, and an O-ring 108 is positioned in the second groove 106. A third groove 110 is provided in the cylinder adjacent the second end and is spaced inwardly therefrom such that a lower flange 112 is provided at the second end of the cylinder 98, and a flexible, foam gasket 114 is provided and mounted in the groove 110, the foam gasket 114 being retained by the flange 112. The cylinder 114 has a longitudinal bore 116 extending through the flange 112 and through the body of the cylinder, the bore 116 extending along the longitudinal center line of the cylinder and terminating just inwardly of the upper groove 100. A transverse bore 118 is provided generally perpendicular to the longitudinal bore 116 and intersecting the longitudinal bore 116 at the end thereof inwardly of the upper groove 100. The longitudinal bore 118 is in fluid communication with a circular passageway 120 which is provided within the block 94.

In the absence of a chromatograph column, the pressure tip system is positioned as illustrated in FIG. 8 such that the weight of the pressure tip system pulls the cylinder vertically downwardly causing the O-ring 104 to seal the top of the passageway 120 from the conduit 96, thus preventing the air flow from entering the vertical passageway 120. Thus, O-ring 104 functions both as a seal and also as a retainer which engages the flange 102 and prevents the cylinder mechanism 98 from dropping downwardly out of the passageway 120 of the block 94.

Figure 9:
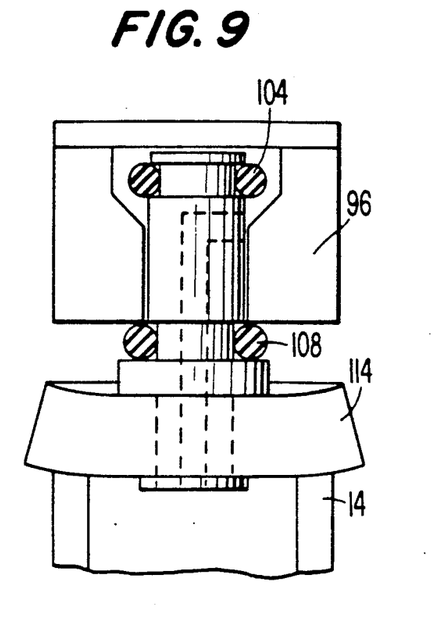
FIG. 9 illustrates a pressure tip associated with a single column in the engaged position.

During the operation of the system of the present invention, the entire pressure system is movable such that cuvettes may be placed in the chassis, and chromatograph columns may be placed in frame 42 within the chassis. Thereafter, the pressure system is moved into position relative to the chromatograph columns and lowered into position such that for each chromatograph column mounted in the rack 42, the reservoir top 14 of the column 10 engages the underside of the foam gasket 114 and pushes upward on the foam gasket such that the foam gasket, while still mounted in the groove 110, moves the cylinder 98 upwardly until the O-ring 108 seals the vertical passageway 120 at the bottom of the block 94. This is illustrated in FIG. 9. Simultaneously pressure between the top of the column 10 and the underside of the foam gasket 114 provides an airtight seal at the top of the column. Lastly, the vertical upward movement of the cylinder 98 moves the upper O-ring 104 clear of the top of the passageway 120. Thus, air pressure through the conduit 96, which is in communication with the output port 83 of the pressure regulator flows through the conduit 96 (for each pressure tip unit), downwardly through the passageway 120 and through the horizontal bore 118 and the vertical bore 116 and thereafter into the top of the chromatography column. A pressure system such as illustrated in FIGS. 8 and 9 is associated with each location in the array of columns.

Thus, it may be appreciated that if a full array of columns is being processed, each column presses upwardly on its respective foam gasket 114 to permit air pressure to flow into the top of the chromatograph column whereas in each position within the array, which is characterized by the absence of a chromatograph column, the pressure system remains in the position of FIG. 8, and no air enters the cylinder 98 associated therewith.

Figure 10:
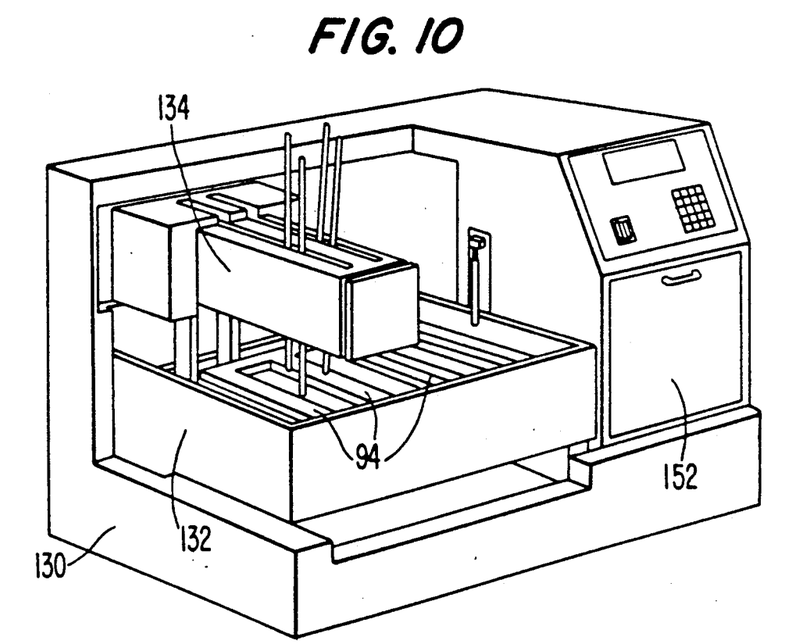
FIG. 10 illustrates, in perspective view, the apparatus of the present invention.

Referring next to FIG. 10, a perspective illustration of the apparatus of the present invention is illustrated. The apparatus of the present invention includes a chassis or frame 130. The frame or rack 42 for the chromatographic columns is mounted within a housing 132 attached to the frame. FIG. 10 also illustrates the five manifolds 94 positioned above the rack 42, the five manifolds or blocks extending from the front to the rear of the housing 132. The cuvettes are positioned below the housing 132 as will be described hereinafter.

Above the housing, a horizontal support block 134 is mounted for movement laterally, i.e., in the "X" direction. Thus, the block 134 moves left and right. Mounted within the block are four discharge needles 136, 137, 138, 139 (see FIG. 17). The needles move as a group in the "Y" direction, i.e., forwardly and rearwardly of the block 134. The needles also move in "Z" or vertical direction. A tray 142 for supporting the cuvettes is slidably mounted under the housing 132 (see FIG. 11).

Figure 11:
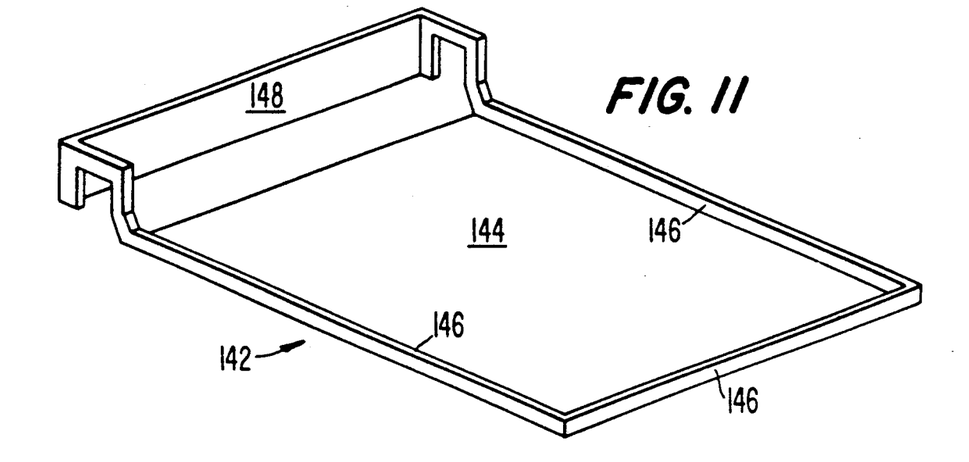
FIG. 11 illustrates, in perspective view, a tray for supporting the cuvettes of the present invention.

FIG. 11 illustrates, in perspective, the tray 142 for the cuvettes, the tray including a generally flat surface or floor 144 upon which the cuvettes are placed, the floor being provided with guide rails 146 on three sides thereof. A handle 148 is provided on the tray for movement of the tray of cuvettes into and out of the apparatus of the present invention. The tray of cuvettes has been removed from FIG. 10 for the purposes of clarity and ease of illustration.

Figure 12:
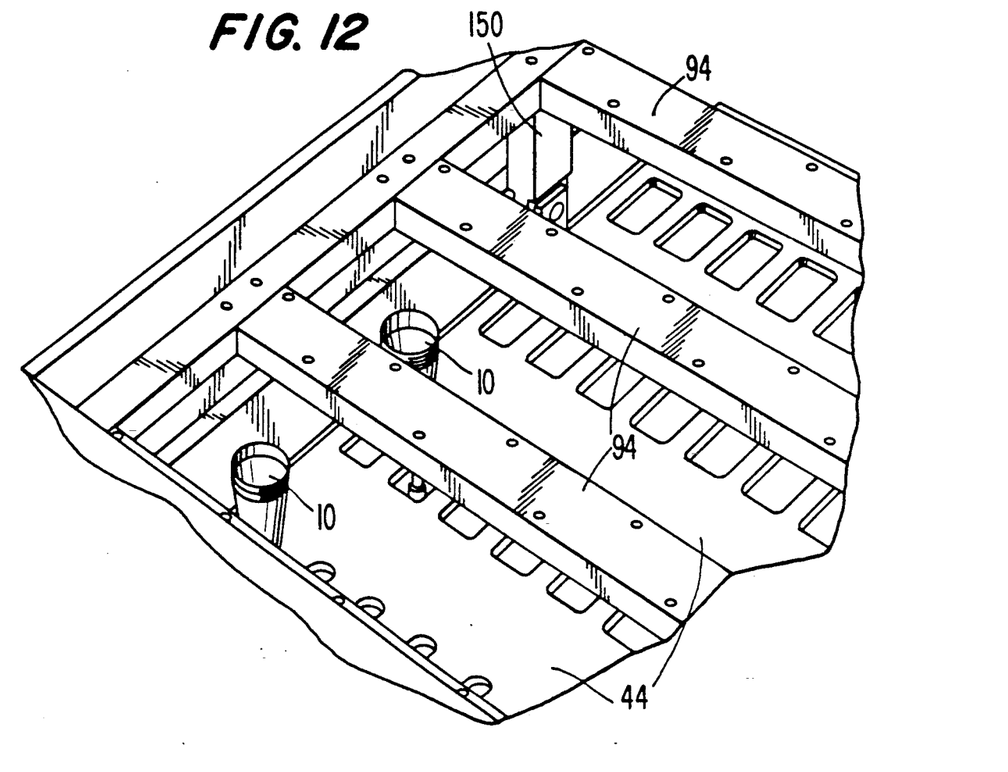
FIG. 12 illustrates a portion of the top of the column rack and a portion of the manifold in a disengaged position as seen from the back of the apparatus.

FIG. 12 illustrates, in perspective form, a rear view portion of the apparatus of the present invention including the movement of the pressure tip system of engagement with the chromatograph columns. In FIG. 12, three of the manifolds or blocks 94 are visible as is the upper plate 44 of the tray 42 with two chromatograph columns 10 in place, one in each of two rows. At the upper right-hand corner of FIG. 12, a vertical link 150 is illustrated. When the system is in the position illustrated in FIG. 12, the needles 136, 137, 138 can access the tops of each of the chromatograph columns such that fluids may be introduced therein.

Figure 13:
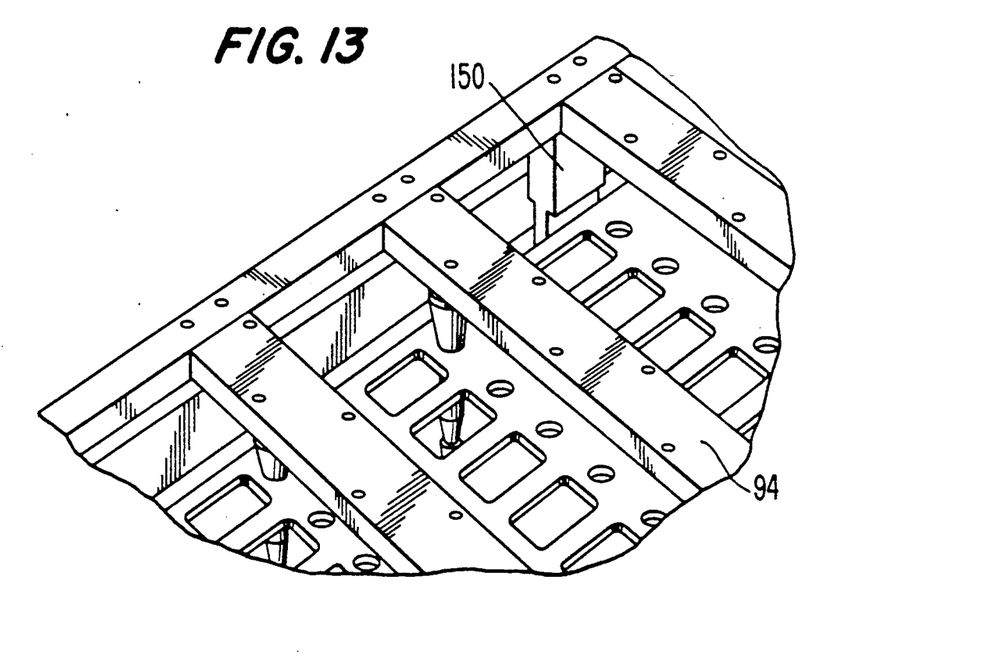
FIG. 13 illustrates the top of the column rack and portion of the manifold of FIG. 12 in an engaged position.

Referring next to FIG. 13, which is a perspective illustration similar to FIG. 12 except that link 150 is now vertical, there has been movement of the manifold blocks such that the manifold blocks 94 are now above the columns and the pressure tip system of FIGS. 8 and 9 is now in contact with the tops of the columns.

Figure 14:
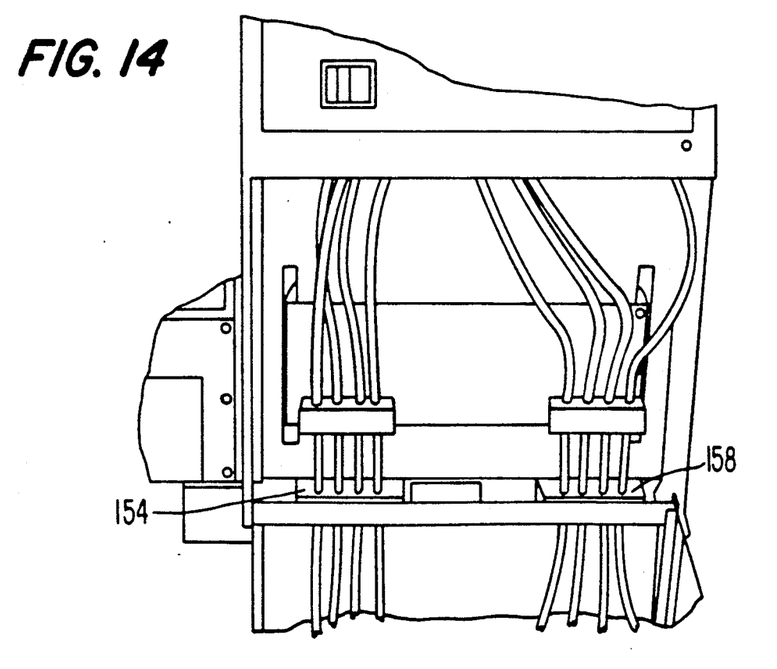
FIG. 14 is a partial front illustration with the door of the apparatus removed.

FIG. 14 illustrates an enlarged, partial front elevation view of the apparatus of the present invention with the door 152 of FIG. 10 open. In this position, a first group of mixing needles 154 is illustrated. There are four such needles, one to be associated with each cell of a single cuvette. After chromatographic separation, the cuvette is moved to the right in FIG. 14 by a stepping motor and is held in position underneath the needles 154 such that the fluid within each cell may be thoroughly mixed. The cuvette is then moved further to the right in FIG. 14 to be scanned by an optical reader 156 (see FIG. 17). After scanning by the optical reader 156, the cuvette advances further to the right under a second group of needles 158 which contain fluid for washing out the cuvette cells.

It was previously indicated that cuvette cell 38d is larger than the other three cuvette cells. This is because in column chromatography, it is common to collect eluates and, in a separate container, dilute a second sample (e.g., of blood or other biological fluid) such that comparative optical density readings may be taken for providing an indication if all of the sample has moved through the chromatograph column. This technique is, of course, well known.

Figure 15:
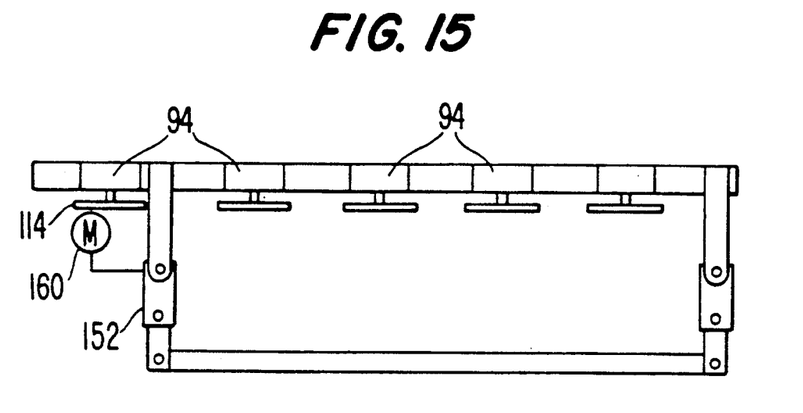
FIG. 15 is a diagrammatic illustration of the motor and linkage for positioning the manifold in the disengaged apart position.

FIG. 15 illustrates, in diagrammatic form, linkage and a motor 160 for moving the manifold system in the retracted position, relative to the tops of the individual chromatograph columns such that reagents, samples and the like may be introduced therein.

Figure 16:
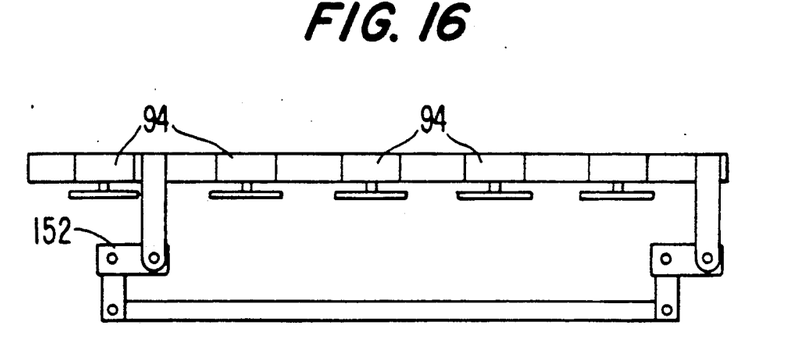
FIG. 16 is a diagrammatic illustration of the motor and linkage for positioning the manifold in the engaged position.

FIG. 16 illustrates, diagrammatically, the linkage and motor system of FIG. 15 in the engaged position, illustrating the 90° rotation of the aforementioned link 150. It should be noted that while FIGS. 12 and 13 provide a rear perspective illustration, FIGS. 15 and 16 provide a front elevation diagrammatic illustration.

Figure 17:
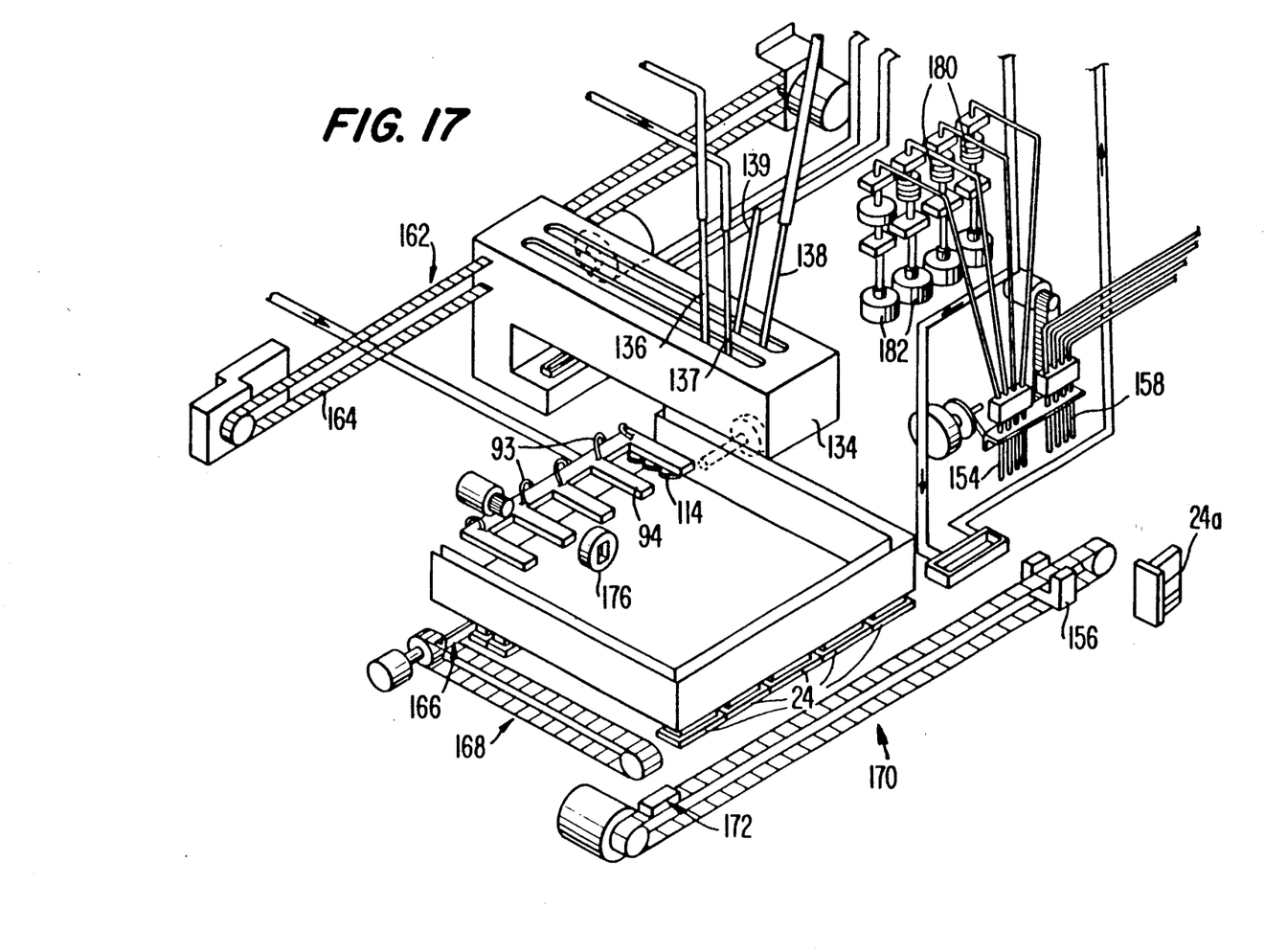
FIG. 17 illustrates, diagrammatically, the apparatus of the present invention including, in general terms, the frame or chassis, the location of various fluid supplies and the location of the optical density reader.

Referring next to FIG. 17, an overall system illustration of the present invention will now be described. Block 134 is illustrated as mounted to a stepping motor system 162 which moves the block 134 laterally through a drive belt 164. The cuvettes are processed from right to left and from front to back as illustrated in FIG. 17. To accomplish this, a bar or fence 166 extends across the width of the housing 132, underneath the housing but above the tray 142, and one end of the bar is connected to a drive mechanism 168. Advancing the drive mechanism 168 moves the bar 166 forwardly such that five cuvettes 24, one from each row, moves forwardly clear of the tray 142 and onto a drive mechanism 170. Drive mechanism 170 includes a pusher block 172 which advances the cuvettes sequentially underneath the mixer needles 154, through the optical reader 156, and thereafter underneath the evacuator needles 158 which are connected through a pump to a waste evacuation system. After the five cuvettes are processed, drive system 168 advances the bar 166 forward, yet another step, such that the next row of five cuvettes may be deposited onto the drive belt 170 and processed sequentially. FIG. 17 also illustrates a cuvette 24a dropping off the drive mechanism after the completion of mixing, reading and evacuation.

It should be further appreciated that as part of the present invention, a cam 176 is provided, illustrated diagrammatically in FIG. 17, which is mounted on a motor such that at the completion of the chromatographic separation, rotation of the motor causes raising and lowering the entire housing 132. This movement causes any drops at the bottom of the tips of the chromatograph columns to drop into the respective cells of the cuvettes.

The three needles 136, 137 and 138, illustrated in FIG. 10 and in FIG. 17, each move in the "Z" direction under influence of motors and thus provide for mixing or agitation of the resin in the column as well as providing conduits for the addition of reagents and/or samples into the columns. In addition, vertical movement of decapper needle 139 provides for removal of the tips from the columns. Thus, needle 139 functions to move spring 62 downwardly.

Reference should also be had to the bellows-motor 180 illustrated in FIG. 17 wherein four bellow systems are illustrated, each associated with one of the needles 154 and each attached to a motor 182. Motor 182 rotates, and an internal threaded nut system converts the rotation motion of the motor 182 into linear motion of the bellows 180 which, in turn, moves the needles 154 vertically for mixing the liquid in the cuvette cells prior to the liquid passing through the optical reader 156.

The bellows-motor arrangement illustrated with respect to the needles or mixer unit 154 may be replicated for movement of the needles 136-140 as they provide controlled, bi-directional movement in small increments.

The foregoing is a complete description of a preferred embodiment of the present invention. The invention automates those steps normally performed by a technician in a manual pipetting operation, and the individual steps, per se, are conventional.

Many changes and modifications may be made without departing from the spirit and scope of the present invention. The invention, therefore, should be limited only by the following claims.

What is claimed is:

1. A system for delivering a constant low pressure to a chromatography column positioned within means for holding an array of chromatography columns comprising:
   a manifold adapted to be connected to a source of low pressure fluid and adapted to be connected to cylinder means having first and second positions and having a fluid path therethrough;
   said first position for preventing fluid from said manifold from entering the fluid path of said cylinder means;
   said second position for providing fluid flow from said manifold through the fluid path of said cylinder means;
   said cylinder means adapted to engage a chromatographic column in a fluid sealing relationship; and
   said cylinder means being normally in said first position and being movable into said second position by contact with said chromatographic column; said second position of said cylinder means thereby allowing said constant low pressure provided to said manifold system to be delivered to said chromatography column.

2. The invention as defined in claim 1 including a plurality of chromatography columns, means for positioning said plurality of chromatographic columns at a first station, said first station including a plurality of column locations, means for positioning a plurality of cuvettes at a second station, said second station having a predetermined spatial orientation relative to said first station, said second station having a plurality of cuvette locations, one cuvette location at said second station associated with a column location at said first station, and wherein said pressure system provides fluid to the first end of each of said columns such that liquids introduced into the first end of each column are eluted through the column into the cuvette associated with the column.

3. The invention as defined in claim 2 wherein said pressure system prevents the flow of fluid in the absence of a chromatographic column from a column location at said first station.

4. The invention as defined in claim 2 wherein the fluid is air.

5. The invention as defined in claim 2 wherein the fluid is maintained at a pressure from between about 3 inches of water to about 8 inches of water.

6. The invention as defined in claim 2 wherein each cuvette includes a plurality of discrete cells, each cell for collecting one or more eluted liquids associated with a single chromatographic column.

7. The invention as defined in claim 2 wherein said pressure system includes a pressure regulator.

8. The invention as defined in claim 7 wherein said pressure regular selectively provides fluid pressure at more than one constant pressure.

9. The invention as defined in claim 2 wherein each column includes a protective cap at said second end; said system further including means for removing the cap from said column.

10. The invention as defined in claim 9 wherein the cap removing means is biased by said column positioning means for removing the cap from the column.

11. The invention as defined in claim 2 wherein each cuvette includes a base having first and second generally planar surfaces;
   a pair of opposed, parallel, spaced apart side walls extending from a first surface to said base;
   a pair of opposed, parallel, spaced apart end walls extending from said first surface of said base generally perpendicularly to said side walls; and at least two interior walls positioned parallel to said end walls and spaced apart therefrom, said interior walls each extending from said first surface and contacting both side walls; said base, side walls, end walls and interior walls defining at least three cells for discrete retention of liquid therein.

12. A method for delivering a constant low pressure to a chromatography column positioned within means for holding an array of chromatography columns comprising:
   providing a manifold adapted to be connected to a source of low pressure fluid;
   providing a pressure cylinder coupled to said manifold and having first and second positions and having a fluid path therethrough;
   said first position for preventing fluid from entering the fluid path of said cylinder;
   said second position for providing fluid flow from said manifold through the fluid path of said cylinder;
   said cylinder being normally in said first position; and
   moving said cylinder from said first position into said second position by contact with a chromatographic column; said second position of said cylinder means thereby allowing said constant low pressure provided to said manifold system to be delivered to said chromatography column.

13. The invention as defined in claim 12 including positioning a plurality of chromatographic columns at a first station, said first station including a plurality of column locations;
   positioning a plurality of cuvettes at a second station, said second station having a predetermined spatial orientation relative to said first station; said second station having a plurality of cuvette locations; one cuvette at said second station associated with a column at said first station; wherein said pressurized fluid is provided to each of said columns for eluting liquids through each column into the cuvette associated with said column, and providing a pressure cylinder associated with each chromatographic column location; and
   preventing the flow of fluid through a specific pressure cylinder in the absence of a chromatographic column at the column location associated therewith.

14. The invention as defined in claim 12 wherein the fluid is air.

15. The invention as defined in claim 12 wherein the fluid is maintained at a pressure from between about 3 inches of water to about 8 inches of water.

16. The invention as defined in claim 13 including providing, as part of each cuvette, a plurality of discrete cells, each cell for collecting one or more eluted liquids associated with a single chromatographic column.

17. The invention as defined in claim 12 including selectively providing fluid pressure at more than one constant pressure.

18. The invention as defined in claim 12 including providing an array of pressure tips each associated with the location for one column, each pressure tip movable from a normally closed position to an open position; and moving the pressure tip from said normally closed position to said open position by contact with a column.

19. The invention as defined in claim 12 wherein each column includes a protective cap at one end; and removing the cap from said column by contacting said cap with a column positioning means.

* * * * *